(12) United States Patent
Kazao

(10) Patent No.: US 10,054,553 B2
(45) Date of Patent: Aug. 21, 2018

(54) VISUAL INSPECTION METHOD FOR LIGHT-EMITTING DEVICE

(71) Applicant: NICHIA CORPORATION, Anan-shi (JP)

(72) Inventor: Kenta Kazao, Tokushima (JP)

(73) Assignee: NICHIA CORPORATION, Anan-shi (JP)

( * ) Notice: Subject to any disclaimer, the term of this patent is extended or adjusted under 35 U.S.C. 154(b) by 14 days.

(21) Appl. No.: 15/210,896

(22) Filed: Jul. 15, 2016

(65) Prior Publication Data

US 2017/0016764 A1    Jan. 19, 2017

(30) Foreign Application Priority Data

Jul. 15, 2015 (JP) .................................. 2015-140978

(51) Int. Cl.
*G01J 1/44* (2006.01)
*G01N 21/95* (2006.01)

(52) U.S. Cl.
CPC .................................. *G01N 21/95* (2013.01)

(58) Field of Classification Search
CPC ...... G01N 21/95; G01N 21/88; G01N 21/956; G01N 21/9501; G01N 21/47; G01N 21/21; G01N 21/4738; G01N 2201/062; G01N 21/474; G01N 25/72; G01N 21/4795; G01N 2021/8864; G01N 2201/061; G01N 2021/4707; G01N 21/896; G01N 21/9054; G01N 2201/0634; G01N 2021/8816; G01N 2021/8829; G01N 2021/8835;
(Continued)

(56) References Cited

U.S. PATENT DOCUMENTS 7,595,653 B2 * 9/2009 Henttonen .............. G01L 27/00
324/750.01
9,224,361 B2 * 12/2015 Song ........................ G09G 3/34
(Continued)

FOREIGN PATENT DOCUMENTS

JP      05-308159      11/1993
JP      06-160286      6/1994
(Continued)

*Primary Examiner* — Mohamed K Amara
(74) *Attorney, Agent, or Firm* — Mori & Ward, LLP

(57) ABSTRACT

A visual inspection method for a light-emitting device includes: providing a light-emitting device having a substrate and a light-emitting portion, the substrate having a substrate upper surface and a substrate bottom surface, the light-emitting portion being provided on the substrate upper surface and having a light-emitting upper surface, a light-emitting lower surface, and a lateral surface which is provided between the light-emitting lower surface and the light-emitting upper surface and which is surrounded by a light shielding member; placing the light-emitting device on an inspection surface so that the substrate bottom surface is opposite to the inspection surface; supplying power to the light-emitting device so that the light-emitting portion emits light from the light-emitting upper surface; and capturing brightness on the inspection surface surrounding an entire outer periphery of the light-emitting device viewed in the height direction while the light-emitting portion emits light.

3 Claims, 5 Drawing Sheets

(58) Field of Classification Search
CPC ....... G01N 2021/558; G01N 2201/063; G01B
11/00; G01B 11/24; G01B 11/25; H01L
33/00; H01L 33/48; H01L 2924/181;
H01L 2924/12041; H01L 21/00; H01L
33/486; H01L 2924/12042; H01L 33/58;
H01L 25/167; H01L 33/52; H01S 5/00;
G01J 2001/4247; G01J 1/00; G01J
1/4228; G01J 1/4257; G01J 1/0403; G01J
1/0411; G01J 1/0422; G01J 1/16; G01J
3/021; G01J 2001/4261; G01J 1/36; G01J
2003/2859; G01J 1/38; G01M 11/00;
G01M 11/30; G01M 3/38; G01M 17/027;
G01M 99/002; G01M 11/0278; G01M
11/31; G01M 11/0242; G06T 7/0004;
G06T 2207/30148; G06T 2207/10016;
F21Y 2115/10
See application file for complete search history.

(56) References Cited

U.S. PATENT DOCUMENTS

| | | | | |
|---|---|---|---|---|
| 2001/0032985 | A1* | 10/2001 | Bhat | H01L 25/0753 257/88 |
| 2005/0007777 | A1* | 1/2005 | Klipstein | F21L 4/005 362/244 |
| 2005/0035311 | A1* | 2/2005 | Asakawa | G01N 21/8806 250/559.16 |
| 2007/0081313 | A1* | 4/2007 | Tanaka | H01L 33/486 361/767 |
| 2009/0136120 | A1* | 5/2009 | Onushkin | G01N 21/95 382/149 |
| 2014/0016310 | A1* | 1/2014 | Xie | F21V 5/007 362/231 |
| 2014/0231821 | A1* | 8/2014 | Fukui | H01L 33/52 257/76 |
| 2015/0001563 | A1* | 1/2015 | Miki | H01L 33/54 257/98 |
| 2015/0371585 | A1* | 12/2015 | Bower | G09G 3/32 345/1.1 |
| 2016/0190397 | A1* | 6/2016 | Lin | H01L 33/486 257/98 |
| 2016/0254214 | A1* | 9/2016 | Makino | H01L 24/97 257/676 |
| 2017/0184256 | A1* | 6/2017 | Horvath | F21K 9/69 |

FOREIGN PATENT DOCUMENTS

| | | | |
|---|---|---|---|
| JP | 08-031901 | | 2/1996 |
| JP | 09-167863 | | 6/1997 |
| JP | 2007078581 A | * | 3/2007 |
| KR | 20140012342 A | * | 2/2014 |

* cited by examiner

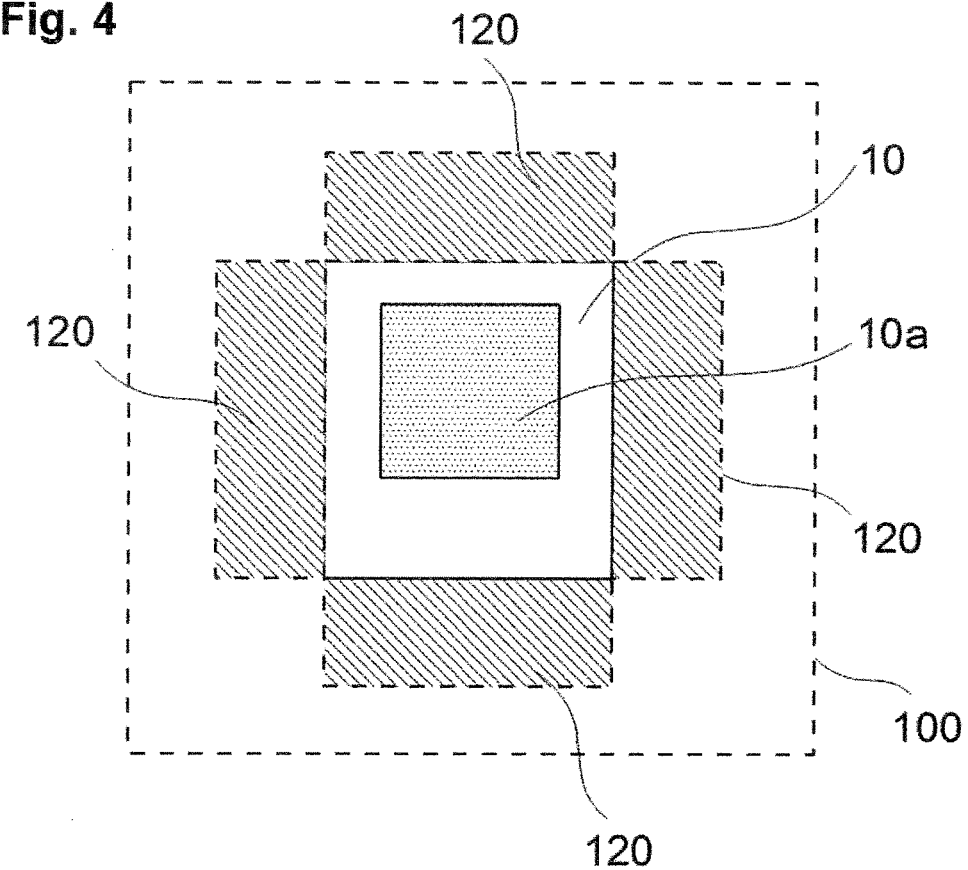

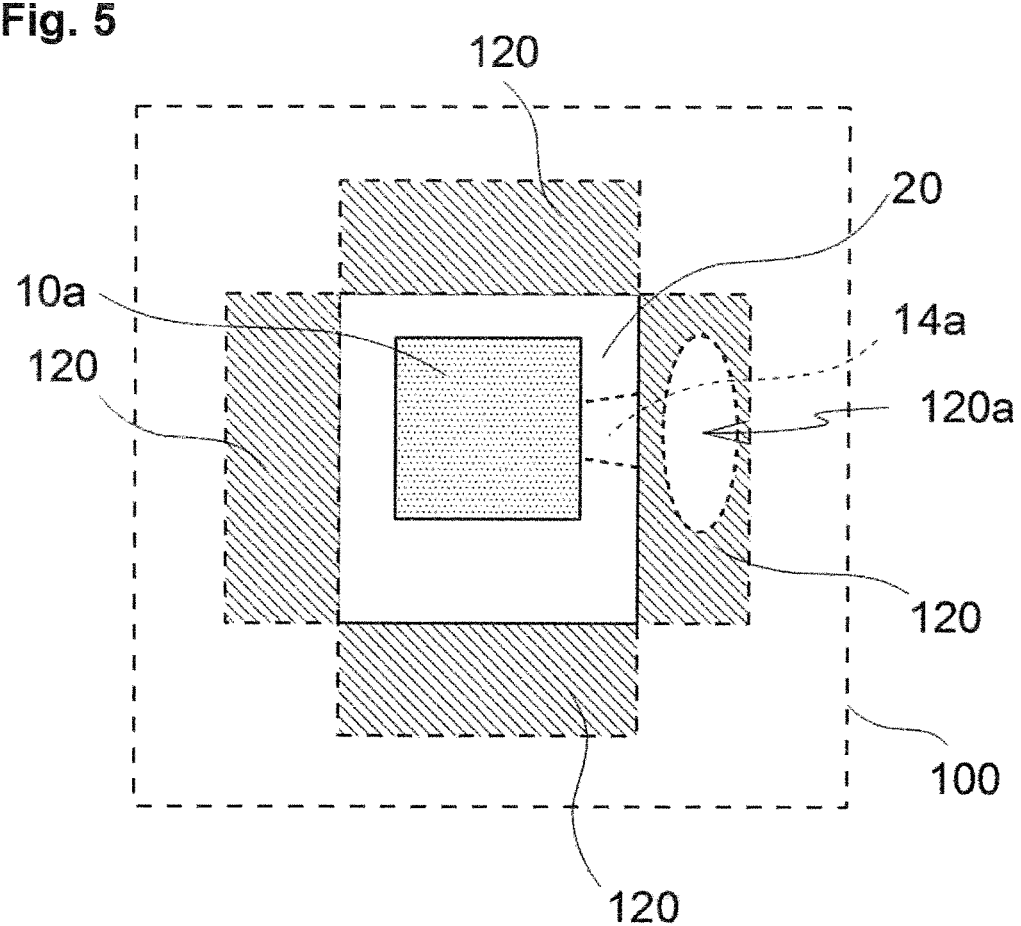

VISUAL INSPECTION METHOD FOR LIGHT-EMITTING DEVICE

CROSS-REFERENCE TO RELATED APPLICATION

This application claims priority to Japanese Patent Application No. 2015-140978 filed on Jul. 15, 2015. The entire disclosure of Japanese Patent Application No. 2015-140978 is hereby incorporated herein by reference.

BACKGROUND

Technical Field

The present invention relates to a visual inspection method for a light-emitting device.

Description of Related Art

Visual inspection of semiconductor packages is performed based on image information of a surface to be observed or based on visual observations. For example, as the methods for inspecting lateral surfaces of the semiconductor package, methods using the information of images captured by cameras arranged with respect to the lateral surfaces is known (for example, see Japanese Unexamined Patent Application Publication No. 1994-160286).

SUMMARY OF THE INVENTION

According to one aspect of the present invention, a visual inspection method for a light-emitting device, includes: providing a light-emitting device having a substrate and a light-emitting portion, the substrate having a substrate upper surface and a substrate bottom surface opposite to the substrate upper surface in a height direction of the light-emitting device, the light-emitting portion being provided on the substrate upper surface and having a light-emitting upper surface, a light-emitting lower surface opposite to the light-emitting upper surface in the height direction, and a lateral surface which is provided between the light-emitting lower surface and the light-emitting upper surface and which is surrounded by a light shielding member, the light-emitting lower surface being opposite to the substrate upper surface in the height direction; placing the light-emitting device on an inspection surface so that the substrate bottom surface is opposite to the inspection surface; supplying power to the light-emitting device so that the light-emitting portion emits light from the light-emitting upper surface; and capturing brightness on the inspection surface surrounding an entire outer periphery of the light-emitting device viewed in the height direction while the light-emitting portion emits light.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 4 is a schematic view to describe the visual inspection method for the light-emitting device according to an embodiment; and FIG. 5 is a schematic view to describe the visual inspection method for the light-emitting device according to an embodiment.

DESCRIPTION OF EMBODIMENTS

Figure 1A:
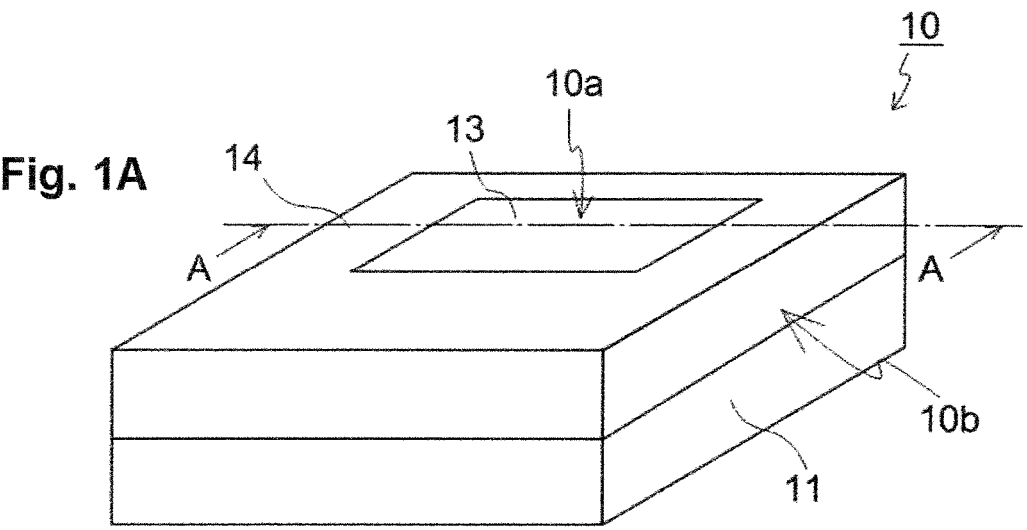
FIG. 1A is a schematic perspective view of a light-emitting device.
Figure 1B:
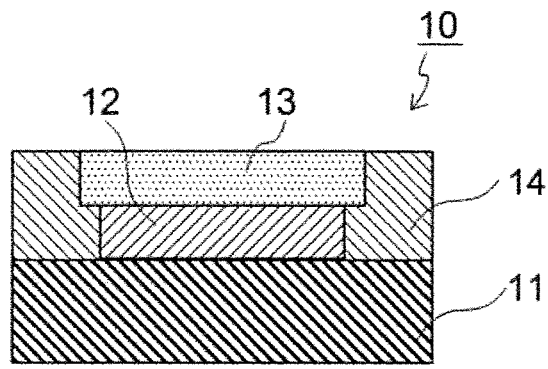
FIG. 1B is a schematic cross-sectional view of the light-emitting device which is taken along line A-A.

The embodiments will now be described with reference to the accompanying drawings, wherein like reference numerals designate corresponding or identical elements throughout the various drawings.

The embodiment of the present invention will be described referring to drawings. Embodiments shown below are intended as illustrative of a visual inspection method for a light-emitting device to give a concrete form to the technical ideas of the present invention, and the visual inspection method for the light-emitting device which is described below is not a limitation to the scope of the present invention.

Also, in the present specification, members disclosed in claims are not limited to members in the embodiments. In particular, unless specifically stated otherwise, sizes, materials, shapes, and relative positions of components described in embodiments are given as an example and not as a limitation to the scope of the present invention. The sizes, or positional relationships of members illustrated in each drawing are occasionally shown exaggerated for clarifying the descriptions. Furthermore, in the descriptions below, the same designations or the same reference numbers denote the same or similar members, and its detailed description is appropriately omitted.

Light-emitting devices to which visual inspection according to an embodiment is performed are illustrated in FIGS. 1A to 2B. Light-emitting devices 10 and 20 each includes a substrate 11, a light-emitting element 12 mounted on the substrate, and a light transmissive member 13 arranged on the light-emitting element 12. Furthermore, the light-emitting devices 10 and 20 each includes a light shielding member 14 covering lateral surfaces of the light-emitting element 12 and lateral surfaces of the light transmissive member 13. That is, the upper surface of the light-emitting device includes a light-emitting portion 10a, which is an upper surface of the light transmissive member 13, and an upper surface of the light shielding member 14 surrounding the light-emitting portion 10a. The light-emitting device 10 does not contain a void, and the light-emitting device 20 contains a void.

Figure 3A:
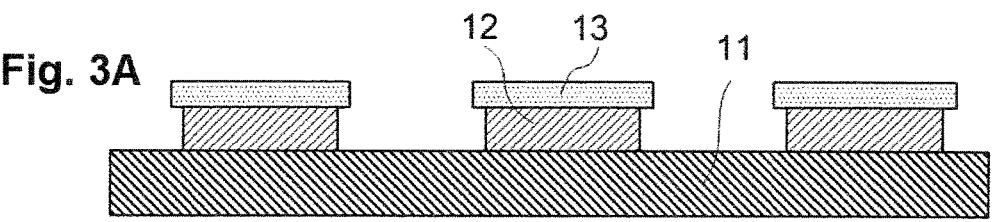
FIG. 3A is a schematic view to illustrate a method for manufacturing the light-emitting device.
Figure 3B:
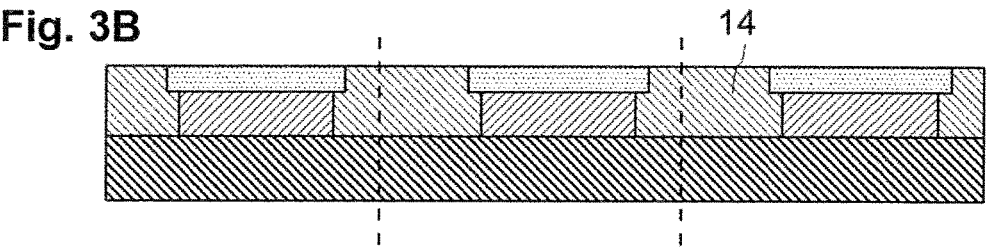
FIG. 3B is a schematic view to illustrate a method for manufacturing the light-emitting device.

The light-emitting devices 10 and 20 described above can be obtained, for example, by a method illustrated in FIGS. 3A and 3B. A plurality of light-emitting elements 12 are arranged on the substrate 11, and the light transmissive member 13 is arranged on the light-emitting element 12. Subsequently, the light shielding member 14 is formed so as to cover the lateral surfaces of the light-emitting element 12 and the lateral surfaces of the light transmissive member 13. Finally, the light shielding member 14 and the substrate 11 are cut at a section where the light-emitting element 12 is not present to perform singulation, so that the light-emitting devices 10 and 20 can be obtained.

Figure 2A:
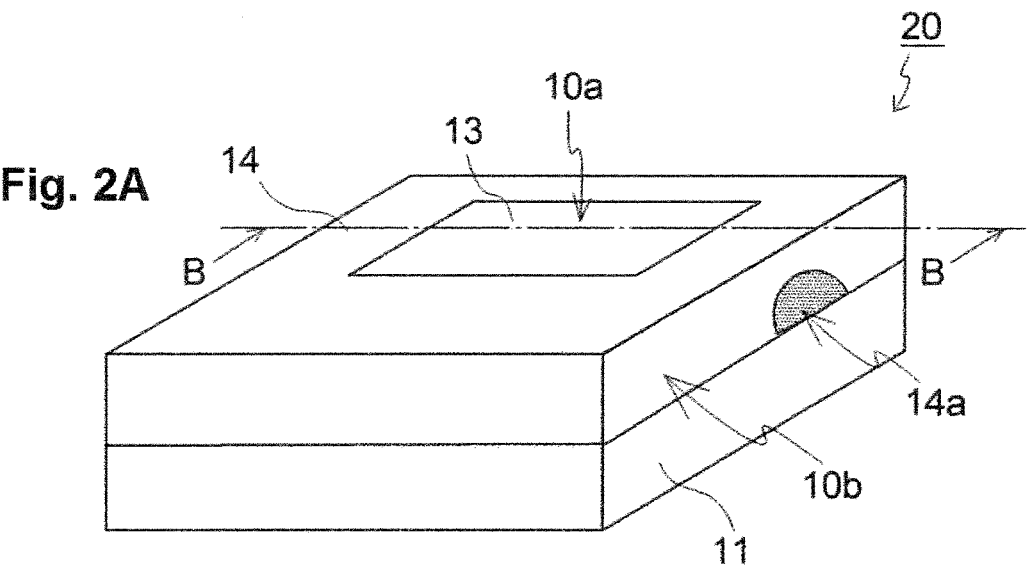
FIG. 2A is a schematic perspective view of the light-emitting device.
Figure 2B:
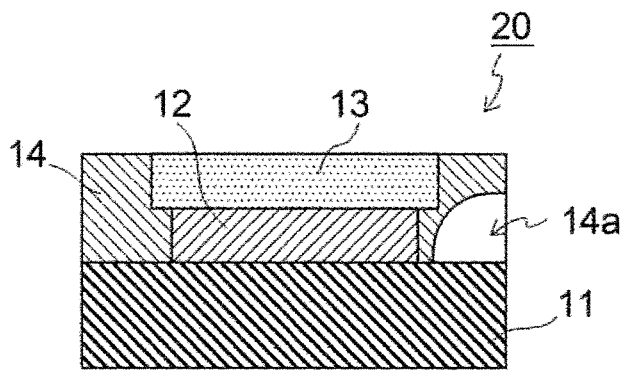
FIG. 2B is a schematic cross-sectional view of the light-emitting device which is taken along line B-B.

As illustrated in FIGS. 2A and 2B, in the interior of the light shielding member 14, which fills a gap between the plurality of light-emitting elements 12 arranged on the substrate 11, a void (an empty portion in which the light shielding member does not exist) 14a is formed. In top view of the light-emitting device, the void 14a inside of the light shielding member 14 is not observed. Also, a portion where the void occurs is not associated with regularity, and the void has a various size. In terms of the position, examples of the void includes a void in contact with the substrate, a void apart from the substrate and in contact with only inside of the light shielding member, a void formed in the vicinity of the center of one lateral surface, a void formed over two lateral surfaces, and the like. Also, in terms of the size, examples of the void further include a void whose area is approximately one forty-fifth to one fourth of the area of the lateral surface of the light-emitting device, a void that reaches the light-emitting element, a void that does not reach the light-emitting element, and the like.

The lateral surface of the light-emitting device 10 is formed by cutting the light shielding member 14, but in the case where the void exists at a cutting position or near the cutting portion, the presence or absence of the void can be easily determined by a method below.

As illustrated in FIGS. 4 and 5, the light-emitting devices 10 and 20, which have been singulated, are each arranged in an image capturing region 100 of an inspection surface. A camera is arranged above the image capturing region 100. The camera is set so that the image capturing region 100 has an area approximately five times larger than the area of the upper surface region of the light-emitting devices 10 and 20 so that its approximate center corresponds to the light-emitting devices 10 and 20.

Electricity is supplied to the light-emitting devices 10 and 20, which causes the light-emitting element (light-emitting portion) to emit light. The light-emitting devices 10 and 20 emitting light are respectively captured by the camera above the light-emitting devices 10 and 20. At this time, the images of peripheral inspection regions 120, which are located the outside of the lateral surfaces of the light-emitting devices 10 and 20, are captured. The image capturing region 100 set as described above is set, in further detail, to have a size such that the image capturing region 100 includes the peripheral inspection regions 120. The peripheral inspection regions 120 can be provided, in plan view, on the outside of one or plural lateral surfaces of the light-emitting device, and in particular, it is preferable that the peripheral inspection regions 120 be provided on the outside of all the lateral surfaces of the light-emitting device.

Upon light emission by the light-emitting portion 10a, in the case where the void does not exist in the light shielding member 14, the peripheral inspection regions 120 is observed to be dark as illustrated in FIG. 4. On the other hand, in the case where the void 14a exists in the light shielding member 14, the light leaks from the void 14a to the outside, so that a bright region 120a is observed in a portion of the peripheral inspection regions 120 as illustrated in FIG. 5. For example, in the case where one void is formed on one lateral surface, one bright region is observed in the peripheral inspection region on the outside of the lateral surface. The larger the void is, the wider the bright region is observed. Also, in the case where a plurality of voids exist and are adjacently arranged, one bright region is observed. In the case where voids are formed on two lateral surfaces, bright areas are observed in the peripheral inspection region on the outside of the lateral surfaces, respectively.

As described above, capturing brightness of the peripheral inspection regions 120 from above the light-emitting devices 10 and 20 in a state where light is emitted by the light-emitting portion 10a allows for checking the external appearance (more specifically, the presence or absence of the void) of the lateral surface of the light-emitting device. That is, with this method, the actual observation of the lateral surface of the light-emitting device can be eliminated, and the external appearance can be easily checked with the camera arranged above the light-emitting device, so that time required for inspection (more specifically, image capturing) can be reduced. Also, in this method, it is not necessary to arrange a camera for capturing an image of the lateral surface of the light-emitting device, so that, for example, even in the case of using an inspection device in which a space in which the camera is to be arranged at the surrounding of the light-emitting device is not present, the inspection for the external appearance of the light-emitting device can be easily performed.

Also, as described above, during the image capturing of the peripheral inspection regions, the state of light emission of the light-emitting portion can be simultaneously imaged. That is, the two inspections can be simultaneously performed. Accordingly, it is possible to perform the visual inspection of the light-emitting device in a short time and suppress the reduction in manufacturing efficiency.

The visual inspection as described above can be applied for inspecting the light-emitting device in which the light-emitting element is mounted in a recess having lateral walls made of the light shielding member, in addition to the light-emitting device obtained in the method described above.

Obviously, numerous modifications and variations of the present invention are possible in light of the above teachings It is therefore to be understood that within the scope of the appended claims, the invention may be practiced otherwise than as specifically described herein.

What is claimed is:

1. A visual inspection method for inspecting a light-emitting device for a void, comprising:
   providing a light-emitting device having a substrate and a light-emitting portion, the substrate having a substrate upper surface and a substrate bottom surface opposite to the substrate upper surface in a height direction of the light-emitting device, the light-emitting portion being provided on the substrate upper surface and having a light-emitting upper surface, a light-emitting lower surface opposite to the light-emitting upper surface in the height direction, and a lateral surface which extends from the light-emitting lower surface to the light-emitting upper surface and which is surrounded around an entire outer periphery by a light shielding member, the light-emitting lower surface being opposite to the substrate upper surface in the height direction;
   placing the light-emitting device on an inspection surface so that the substrate bottom surface is opposite to the inspection surface;
   supplying power to the light-emitting device so that the light-emitting portion emits light from the light-emitting upper surface; and
   capturing brightness on the inspection surface surrounding an entire outer periphery of the light-emitting device viewed in the height direction while the light-emitting portion emits light, the brightness being due to the void in a body of the light shielding member.

2. The visual inspection method according to claim 1, wherein the light emitting device is placed on the inspection surface and then power is supplied to the light emitting device.

3. The visual inspection method according to claim 1, wherein the brightness on the inspection surface is captured from right above the light-emitting device in the height direction.

* * * * *